United States Patent
Chiou et al.

(10) Patent No.: US 7,875,479 B2
(45) Date of Patent: Jan. 25, 2011

(54) INTEGRATION STRUCTURE OF SEMICONDUCTOR CIRCUIT AND MICROPROBE SENSING ELEMENTS AND METHOD FOR FABRICATING THE SAME

(75) Inventors: Jin-Chern Chiou, Hsinchu (TW); Chih-Wei Chang, Yangmei Township, Taoyuan County (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 12/382,587

(22) Filed: Mar. 19, 2009

(65) Prior Publication Data

US 2009/0283867 A1 Nov. 19, 2009

(30) Foreign Application Priority Data

May 13, 2008 (TW) ............... 97117512 A

(51) Int. Cl.
*H01L 21/00* (2006.01)
*H01L 23/48* (2006.01)
*H01L 23/52* (2006.01)

(52) U.S. Cl. .................. 438/48; 438/667; 257/745; 257/E23.01; 257/E21.597; 257/E21.483

(58) Field of Classification Search ............ 438/48, 438/667; 257/745, E21.597, E21.483, E21.486, 257/E23.01

See application file for complete search history.

(56) References Cited

U.S. PATENT DOCUMENTS 5,838,005 A * 11/1998 Majumdar et al. ........... 850/9
6,479,817 B1 * 11/2002 Yedur et al. ................ 850/6
6,838,763 B2 * 1/2005 Ahn et al. ................. 257/698
7,160,752 B2    1/2007 Ouellet et al.
7,208,809 B2    4/2007 Urano et al.
2006/0278825 A1 * 12/2006 van der Weide et al. ...... 250/306

OTHER PUBLICATIONS

Anwar Sadad, Hongwei Qu, Chuanzhao Yu, Jiann S. Yuan, Huikai Xie; Low-Power CMOS Wireless MEMS Motion Sensor for Physiological Activity Monitoring; IEEE Transactions on Circuits and Systems-1: Regular Papers, vol. 52, No. 12, Dec. 2005, pp. 2539-2551.

Ann Witvrouw; CMOS-MEMS Integration: Why, How and What?; Computer-Aided Design, 2006, ICCAD, '06, IEEE/ACM International Conference, Nov. 5-9, 2006, pp. 826-827.

* cited by examiner

*Primary Examiner*—Caridad M Everhart
(74) *Attorney, Agent, or Firm*—Rosenberg, Klein & Lee

(57) ABSTRACT

The present invention discloses an integration structure of a semiconductor circuit and microprobe sensing elements and a method for fabricating the same. In the method of the present invention, a semiconductor circuit is fabricated on one surface of a semiconductor substrate, and the other surface of the semiconductor substrate is etched to form a microprobe structure for detect physiological signals. Next, a deposition method is used to sequentially form an electrical isolated layer and an electrical conductive layer on the microprobes. Then, an electrical conductive material is used to electrically connect the electrical conductive layer with the electrical pads of the semiconductor circuit. Thus is achieved the integration of a semiconductor circuit and microprobe sensing elements in an identical semiconductor substrate with the problem of electric electrical isolated being solved simultaneously. Thereby, the voltage level detected by the microprobes will not interfere with the operation of the semiconductor circuit.

21 Claims, 5 Drawing Sheets

US 7,875,479 B2

INTEGRATION STRUCTURE OF SEMICONDUCTOR CIRCUIT AND MICROPROBE SENSING ELEMENTS AND METHOD FOR FABRICATING THE SAME

BACKGROUND OF THE INVENTION

1. Field of the Invention

The present invention relates to an integration structure of semiconductor elements and microelectromechanical elements, particularly to an integration structure of a semiconductor circuit and microprobe sensing elements and a method for fabricating the same.

2. Description of the Related Art

The conventional CMOS-MEMS (MicroElectroMechanical System) integration technology includes the semiconductor process and the microelectromechanical process. The semiconductor process fabricates integrated circuits on the front surface of a silicon wafer. The microelectromechanical process fabricates floating sensing elements via etching or joins sensing elements and actuating elements via deposition.

A U.S. Pat. No. 7,208,809 discloses a "Semiconductor Device Having MEMS", wherein micromirrors, drivers and sensors are fabricated on the rear side of a semiconductor circuit. The sensors are fabricated with an elaborate and complicated surface micromachining method, which needs extra deposition films and photolithographic processes.

A U.S. Pat. No. 7,160,752 discloses a "Fabrication Method of Advanced Silicon-Based MEMS Device", which uses a joining technology to fabricate microelectromechanical actuators and sensors beside a semiconductor circuit. The method needs an alignment technology additionally. Further, the method needs high-precision fabrication processes and expensive apparatuses, but the reliability there of the method is poor.

SUMMARY OF THE INVENTION

The primary objective of the present invention is to provide an integration structure of a semiconductor circuit and microprobe sensing elements and a method for fabricating the same, wherein a semiconductor circuit and microprobe physiological sensors respectively fabricated on two sides of a semiconductor substrate are integrated to promote the integration and reliability of the heterogeneous systems.

Another objective of the present invention is to provide an integration structure of a semiconductor circuit and microprobe sensing elements and a method for fabricating the same, which can solve the problem of electric insulation without using any additional packaging technology when a semiconductor circuit and microelectromechanical sensing elements are fabricated on an identical semiconductor substrate.

To achieve the abovementioned objectives, the present invention proposes an integration structure of a semiconductor circuit and microprobe sensing elements and a method for fabricating the same. In the method of the present invention, a semiconductor circuit and a microprobe structure are respectively fabricated on two surfaces of a semiconductor substrate. The semiconductor circuit has a plurality of electrical pads. The microprobe structure is directly fabricated on the semiconductor substrate with an etching method without using any additional substrate, and the semiconductor substrate is also etched to form through holes penetrating two surfaces thereof. An insulation layer and an electrical conductive layer are sequentially formed on the microprobes with a deposition method. Then, an electrical conductive material is used to connect the electrical pads of the semiconductor circuit and the electrical conductive layers inside the through holes to achieve the integration of the semiconductor circuit and the microprobe sensing elements.

Via a packaging method, the present invention may alternatively fabricate the electrical conductive material into electrical conductive wires or another electrical conductive layer to electrically connect the electrical conductive layer and the electrical pads respectively on two surfaces of the semiconductor substrate. In this embodiment, none through hole is formed in the semiconductor substrate.

Below, the embodiments are described in detail in cooperation with the drawings to make easily understood the objectives, characteristics and functions of the present invention.

DETAILED DESCRIPTION OF THE INVENTION

Refer to FIGS. 1A-1G sectional views schematically showing the method for fabricating an integration structure of a semiconductor circuit and microprobe sensing elements according to one embodiment of the present invention.

Figure 1A:
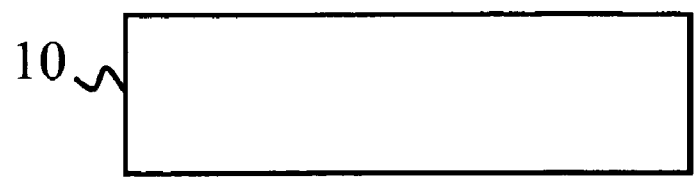
FIGS. 1A-1G are sectional views schematically showing the method for fabricating an integration structure of a semiconductor circuit and microprobe sensing elements according to one embodiment of the present invention.

As shown in FIG. 1A, a semiconductor substrate is provided. The semiconductor substrate is a substrate made of a material for an IC substrate, such as a silicon chip 10 from a silicon wafer or a substrate made of an III-V group semiconductor material.

Figure 1B:
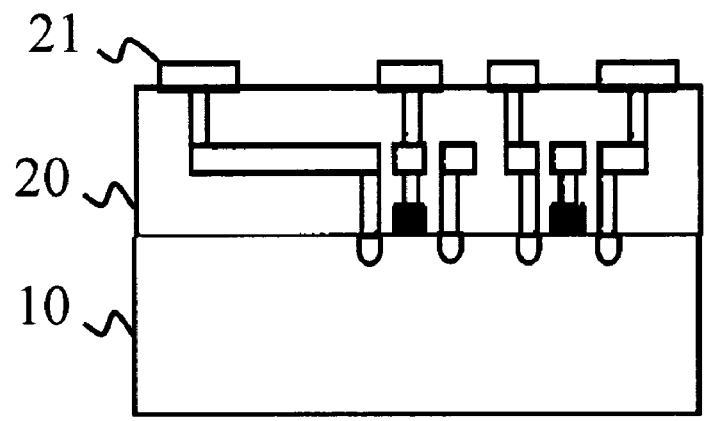

As shown in FIG. 1B, a circuit 20 is formed on the silicon chip 10. The circuit 20 includes a plurality of electrical pads 21. A silicon chip usually has a silicon layer with a thickness of 300-500 μm on the opposite surface thereof. Herein, the surface having the circuit 20 is defined to be the first surface, and the opposite surface is defined to be the second surface.

Figure 1C:
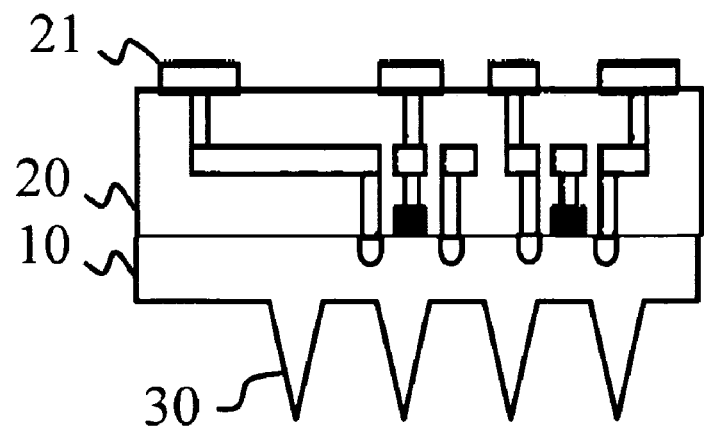

As shown in FIG. 1C, a photolithographic method and an etching method are used to fabricate a microprobe structure 30 on the second surface of the silicon chip 10 having the completed circuit 20. The microprobe structure 30 is used to detect physiological signals and includes a single microprobe or a plurality of microprobes. If the microprobe structure 30 has a plurality of microprobes, the microprobes are arranged into an array. In this embodiment, the etching method may be a wet etching method, a dry gas etching method, an ion reaction etching method, or an electrochemical etching method.

Alternatively, the steps of FIG. 1C can be performed before the step of FIG. 1B. In other words, the microprobe structure 30 is fabricated before the fabrication of the circuit 20.

Figure 1D:
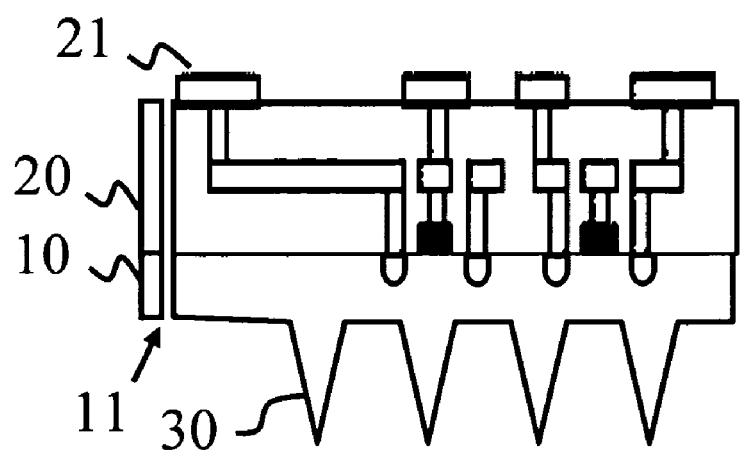

As shown in FIG. 1D, a photolithographic method and an etching method are used to fabricate at least one through hole 11, which penetrates the first and second surfaces of the silicon chip 10 and is used for electric conduction. The silicon chip 10 may have a single through hole 11 or a plurality of through holes 11.

Figure 1E:
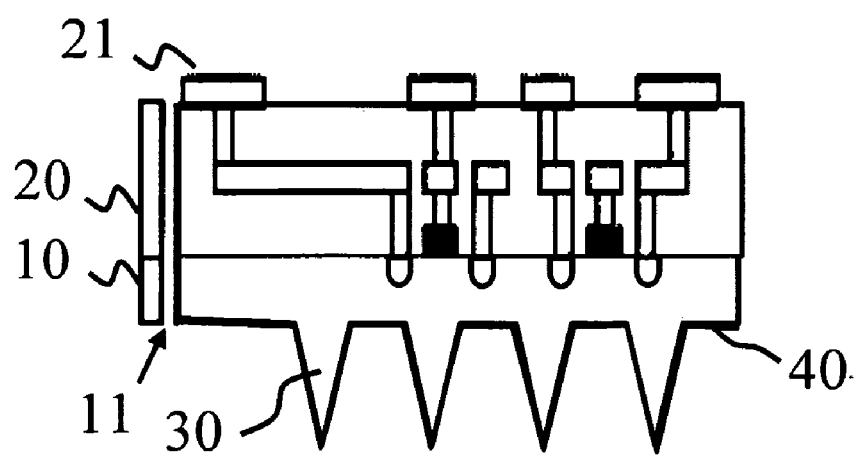

As shown in FIG. 1E, a film deposition method is used to deposit an insulation layer 40 on the second surface. The through hole 11 penetrating the first and second surfaces of the silicon chip 10 is also coated with the insulation layer 40. The insulation layer 40 may be made of any electric-insulation material.

Figure 1F:
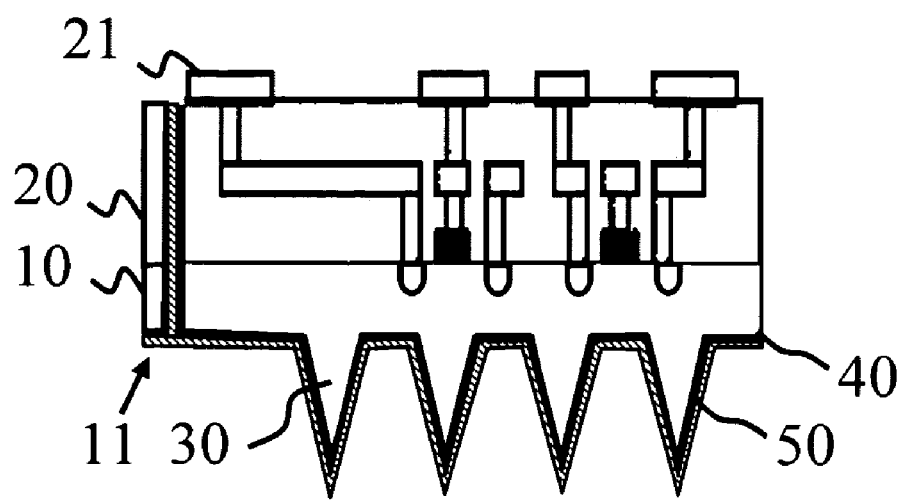

As shown in FIG. 1F, an electrical conductive layer 50 is deposited on the insulation layer 40, and the electrical conductive layer 50 is also deposited on the insulation layer 40 inside the through hole 11. Thereby, the through hole 11 has an electric conduction function.

The insulation layer 40 and the electrical conductive layer 50 are fabricated with a chemical vapor deposition method, a physical vapor deposition method, a chemical liquid deposition method, a physical liquid deposition method, an electroplating method, an electro-forming method, or an ALD (Atomic Layer Deposition) method.

Figure 1G:
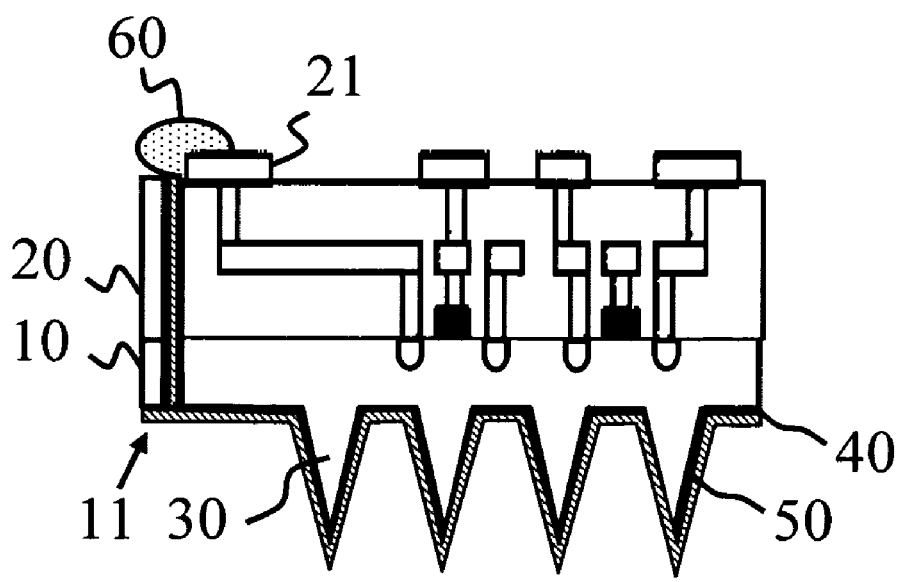

As shown in FIG. 1G, an electrical conductive material 60, such as a silver paste or a solder bump, is used to connect the electrical pad 21 with the electrical conductive layer 50 inside the through hole 11 to complete the integration structure of the present invention.

In this embodiment, the through hole is used to electrically connect two surfaces of the silicon chip, and an insulation layer is deposited beforehand to prevent the physiological signal voltage level from affecting the operation of the circuit. In the conventional technology, an additional substrate is usually used to electrically separate and connect the circuit and MEMS elements both fabricated on semiconductor substrates. However, the present invention can realize the circuit and MEMS elements on an identical semiconductor substrate.

Figure 2:
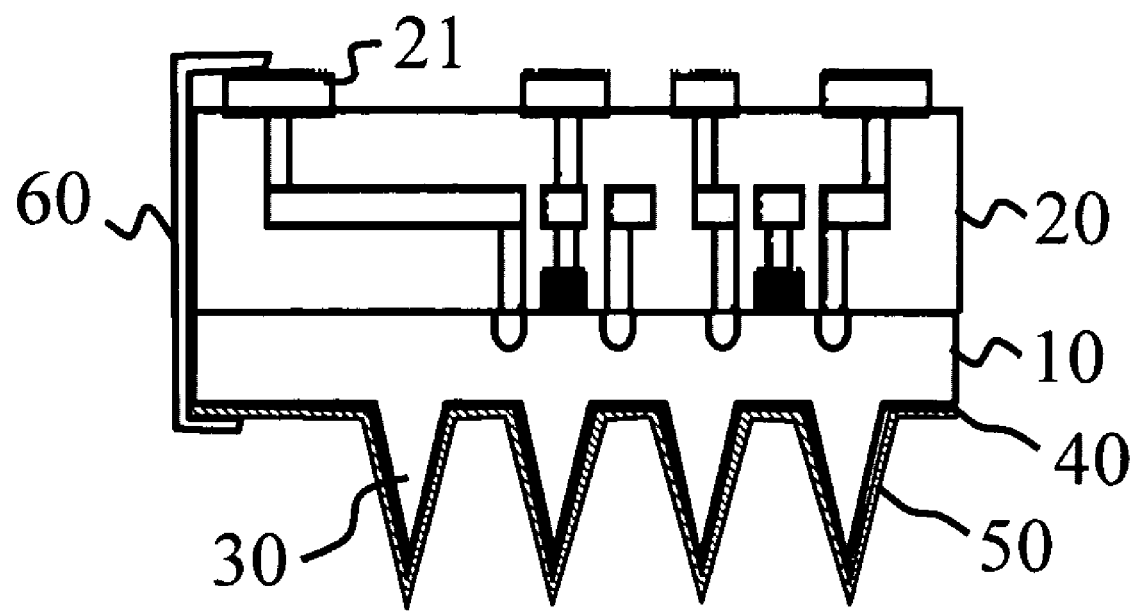
FIG. 2 a sectional view schematically showing an integration structure of a semiconductor circuit and microprobe sensing elements according to another embodiment of the present invention.
Figure 3:
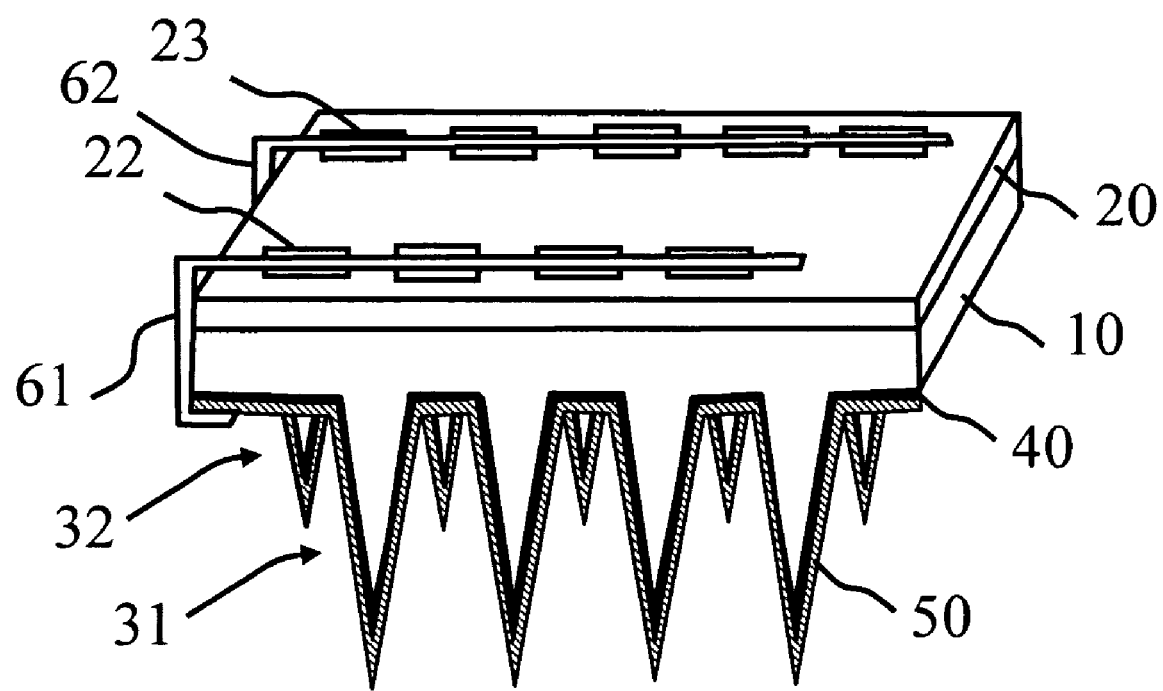
FIG. 3 is a perspective view of an integration structure of a semiconductor circuit and microprobe sensing elements with the electrical conductive material in form of a plurality of wires according to a further embodiment of the present invention.

Refer to FIG. 2 for an integration structure of a semiconductor circuit and microprobe sensing elements according to another-embodiment of the present invention. After the circuit and the microprobe sensing elements are respectively fabricated in the steps of FIG. 1B and FIG. 1C, none through hole is fabricated, but an insulation layer and an electrical conductive layer are directly formed on the second surface of the silicon chip. Then, a packaging method is used to electrically connect the electrical pads on the first surface and the electrical conductive layer on the second surface with an electrical conductive material. The electrical conductive material used to electrically connecting the two surfaces of the silicon substrate may be in form of a single wire, a plurality of wires or a coating to electrically connect a single microprobe, a group of microprobes or the total microprobe structure to the corresponding electrical pads. Refer to FIG. 3 a perspective view of an integration structure of a semiconductor circuit and microprobe sensing elements according to a further embodiment of the present invention, wherein two microprobe groups 31 and 32 are electrically connected to the corresponding electrical pad groups 22 and 23 with an electrical conductive material in form of wires 61 and 62.

In conclusion, the present invention discloses an integration structure of a semiconductor circuit and microprobe sensing elements and a method for fabricating the same, wherein a semiconductor substrate is used as the bulk of a semiconductor circuit and microprobe sensing elements, and a bulk micromachining method is used to fabricate the semiconductor circuit and microprobe sensing elements on the same semiconductor chip and integrate them on the same semiconductor chip with the problem of electric insulation being solved simultaneously. Thus, the present invention is an approach to achieve an SOC (System on Chip) design.

The embodiments described above are only to exemplify the present invention but not to limit the scope of the present invention. Any equivalent modification or variation according to the spirit of the present invention is to be also included within the scope of the present invention, which is based on the claims stated below.

What is claimed is:

1. An integration structure of a semiconductor circuit and microprobe sensing elements, comprising;
    a semiconductor substrate having a first surface and a second surface, wherein said first surface has a circuit containing a plurality of electrical pads, and said second surface is etched to form at least one microprobe;
    an electrical isolated layer formed on said microprobe and said electrical isolated layer conforming to the entire surface of said microprobe;
    an electrical conductive layer formed on said electrical isolated layer and said electrical conductive layer conforming to the entire surface of said electrical isolated layer; and
    an electrical conductive material connecting said electrical conductive layer and said electrical pads.

2. An integration structure of a semiconductor circuit and microprobe sensing elements, comprising:
    a semiconductor substrate having a first surface and a second surface, wherein said first surface has a circuit containing a plurality of electrical pads, and said second surface is etched to form at least one microprobe;
    an electrical isolated layer formed on said microprobe;
    an electrical conductive layer formed on said electrical isolated layer; and
    an electrical conductive material connecting said electrical conductive layer and said electrical pads;
    wherein said semiconductor substrate is made of a III-V group material.

3. The integration structure of a semiconductor circuit and microprobe sensing elements of claim 2, wherein said electrical conductive material is arranged on a periphery of said semiconductor substrate and fabricated into a single electrical conductive wire, a plurality of electrical conductive wires, or another electrical conductive layer.

4. The integration structure of a semiconductor circuit and microprobe sensing elements of claim 2, wherein said electrical pads are solder bumps or made of a silver paste.

5. The integration structure of a semiconductor circuit and microprobe sensing elements of claim 2, wherein said semiconductor substrate further comprises a through hole penetrating said first surface and said second surface; said electrical isolated layer is formed on an inner surface of said through hole; said electrical conductive layer is formed on a surface of said electrical isolated layer on said inner surface of said through hole to enable said through hole to perform an electrical conductive function.

6. The integration structure of a semiconductor circuit and microprobe sensing elements of claim 3, wherein said electrical conductive material is a silver paste or a solder bump.

7. The integration structure of a semiconductor circuit and microprobe sensing elements of claim 2, wherein said second surface is etched to form a plurality of said microprobes.

8. The integration structure of a semiconductor circuit and microprobe sensing elements of claim 7, wherein said microprobes are arranged into a microprobe array.

9. The integration structure of a semiconductor circuit and microprobe sensing elements of claim 7, wherein said microprobes are divided into several groups; each said group is electrically connected to corresponding said electrical pads via said electrical conductive material.

10. A method for fabricating an integration structure of a semiconductor circuit and microprobe sensing elements, comprising steps:
   providing a semiconductor substrate having a first surface and a second surface;
   forming a circuit on said first surface of said semiconductor substrate, wherein said circuit has a plurality of electrical pads; and forming at least one microprobe on said second surface of said semiconductor substrate with an etching method;
   sequentially forming an electrical isolated layer on said microprobe and an electrical conductive layer on said electrical isolated layer with a deposition method; and
   using an electrical conductive material to connect said electrical conductive layer and said electrical pads;
   wherein said semiconductor substrate is made of an III-V group material.

11. The method for fabricating an integration structure of a semiconductor circuit and microprobe sensing elements of claim 10, wherein said etching method is a wet etching method, a dry gas etching method, an ion reaction etching method, or an electrochemical etching method.

12. The method for fabricating an integration structure of a semiconductor circuit and microprobe sensing elements of claim 10, herein said electrical conductive material is arranged on a periphery of said semiconductor substrate and fabricated into a single electrical conductive wire, a plurality of electrical conductive wires, or another electrical conductive layer.

13. The method for fabricating an integration structure of a semiconductor circuit and microprobe sensing elements of claim 10, wherein said electrical pads are solder bumps or made of a silver paste.

14. The method for fabricating an integration structure of a semiconductor circuit and microprobe sensing elements of claim 10, wherein said deposition method is a chemical vapor deposition method, a physical vapor deposition method, a chemical liquid deposition method, a physical liquid deposition method, an electroplating method, an electro-forming method, or an ALD (Atomic Layer Deposition) method.

15. The method for fabricating an integration structure of a semiconductor circuit and microprobe sensing elements of claim 10 further comprising a step of using an etching method to form at least one through hole penetrating said first surface and said second surface after said circuit and said microprobe have been formed.

16. The method for fabricating an integration structure of a semiconductor circuit and microprobe sensing elements of claim 15, wherein said etching method is a wet etching method, a dry gas etching method, an ion reaction etching method, or an electrochemical etching method.

17. The method for fabricating an integration structure of a semiconductor circuit and microprobe sensing elements of claim 15, wherein during forming said electrical isolated layer on said microprobe and said electrical conductive layer on said electrical isolated layer, said electrical isolated layer is formed on an inner surface of said through hole, and said electric-conductor layer is formed on a surface of said electrical isolated layer on said inner surface of said through hole to enable said through hole to perform an electrical conductive function.

18. The method for fabricating an integration structure of a semiconductor circuit and microprobe sensing elements of claim 17, wherein said electrical conductive material is a silver paste or a solder bump.

19. The method for fabricating an integration structure of a semiconductor circuit and microprobe sensing elements of claim 10, wherein said second surface is etched to form a plurality of said microprobes.

20. The method for fabricating an integration structure of a semiconductor circuit and microprobe sensing elements of claim 19, wherein said microprobes are arranged into a microprobe array.

21. The method for fabricating an integration structure of a semiconductor circuit and microprobe sensing elements of claim 19, wherein during connecting said electrical conductive layer and said electrical pads, said microprobes are divided into several groups; each said group is electrically connected to corresponding said electrical pads via said electrical conductive material.

* * * * *